United States Patent [19]
Elliott

[11] Patent Number: 5,569,265
[45] Date of Patent: *Oct. 29, 1996

[54] OBSTETRIC BONNET FOR ASSISTING CHILDBIRTH

[75] Inventor: Byron D. Elliott, San Antonio, Tex.

[73] Assignee: Board Of Regents, The University Of Texas System, Austin, Tex.

[*] Notice: The term of this patent shall not extend beyond the expiration date of Pat. No. 5,507,752.

[21] Appl. No.: 372,606

[22] Filed: Jan. 13, 1995

Related U.S. Application Data

[63] Continuation of Ser. No. 928,131, Aug. 10, 1992, Pat. No. 5,507,752, which is a continuation of Ser. No. 578,819, Sep. 6, 1990, abandoned.

[51] Int. Cl.$^6$ .................................................. A61B 17/42
[52] U.S. Cl. ................................. 606/123; 606/122
[58] Field of Search ................................. 606/123, 122

[56] References Cited

U.S. PATENT DOCUMENTS 2,227,673   1/1941   Price .................................. 606/123
4,730,617   3/1988   King .................................. 606/123

FOREIGN PATENT DOCUMENTS 62846   6/1892   Germany .
839518   6/1981   U.S.S.R. ............................. 606/123

*Primary Examiner*—Michael H. Thaler
*Attorney, Agent, or Firm*—Arnold, White & Durkee

[57] ABSTRACT

Flexible, collapsible, dome or cylinder-shaped bonnet that provides a substantially airtight fit to a fetal head and utilizes frictional and internally-created vacuum forces for assisting childbirth. The bonnet is manually inserted and rolled over the cranium of the fetus, stopping short of the eyes and the ears. Friction and internally created vacuum forces are created when the bonnet is pulled, thus securing the bonnet to the fetus's head and allowing orientation and delivery. The device is comprised of a dome or cylinder-shaped body made of a collapsible elastic material, an optional raised "lip" located on the exterior of the open end, and may have a mechanical extension attached to the closed end. System embodiments allow for the attachment to the exterior of the closed end grommets and/or mechanical extensions that will irreversibly stretch, lengthen, and expose warning alerts in the event that excessive longitudinal force is applied. The bonnet is a significant improvement because it allows a firmer grip on the fetus' head with less danger of damage to either the mother or the fetus. Thus traction and rotational forces may be safely applied to a fetus without the need to use forceps or hard suction cups.

15 Claims, 8 Drawing Sheets

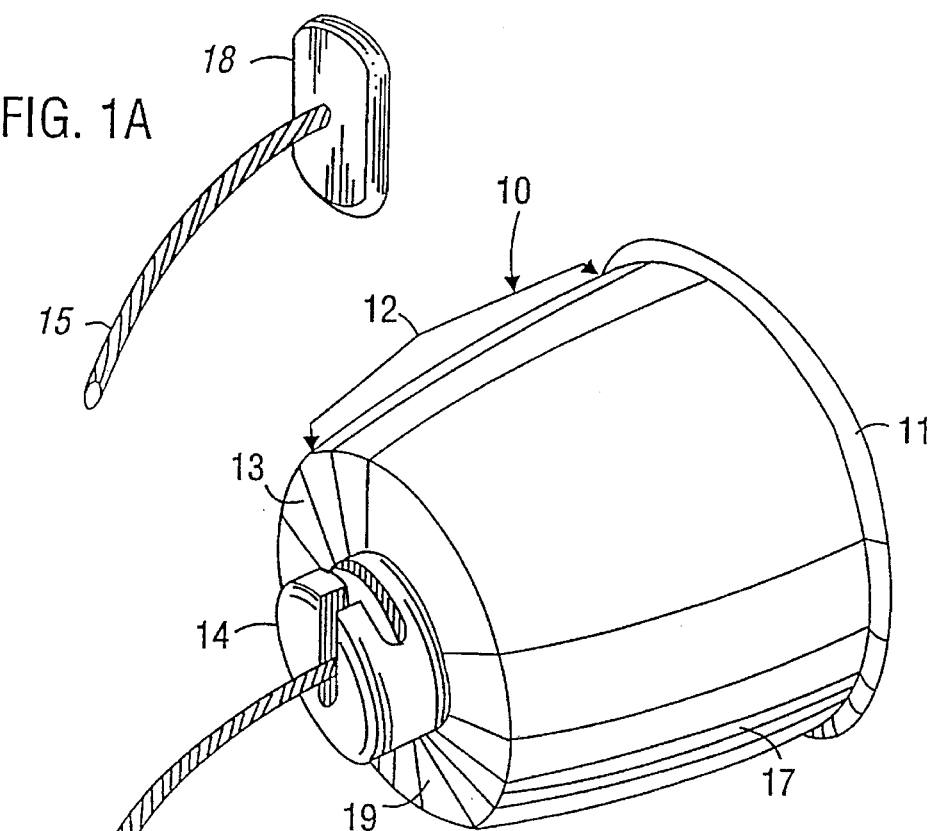
FIG. 1A
FIG. 1
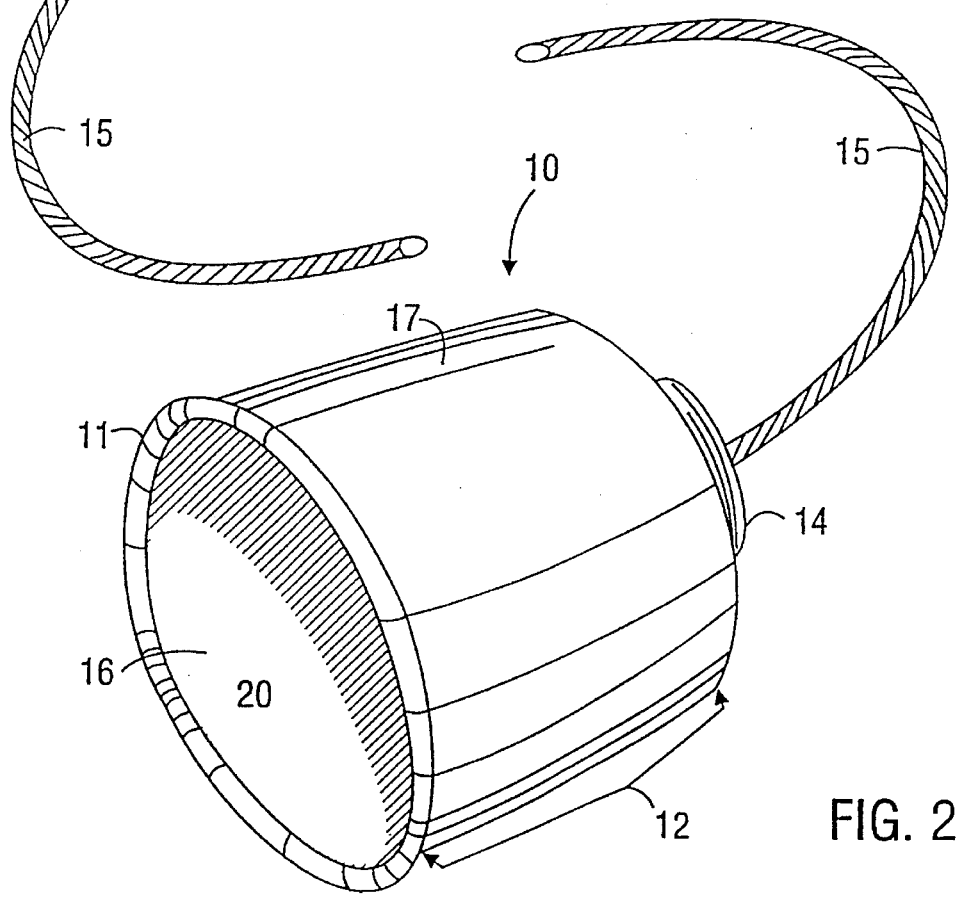
FIG. 2

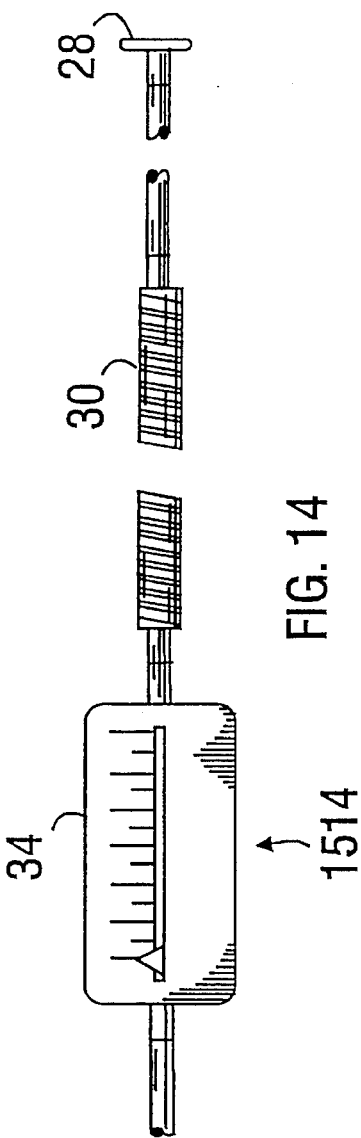
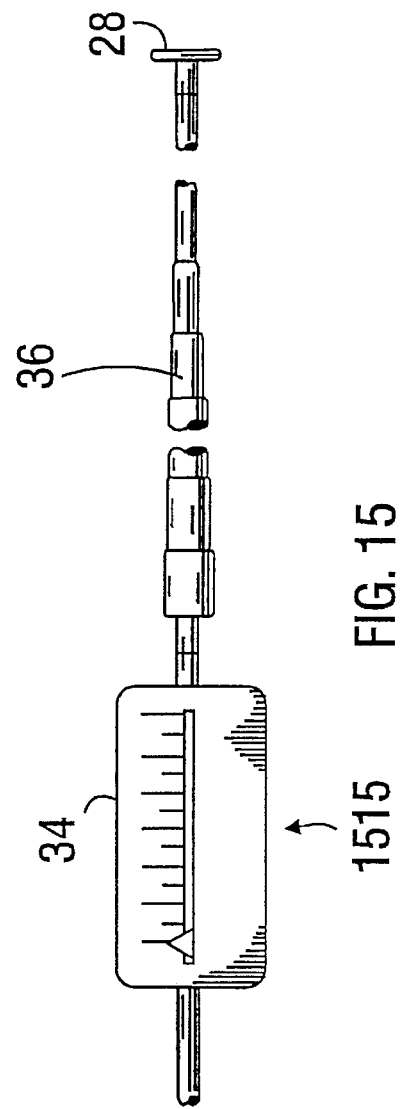
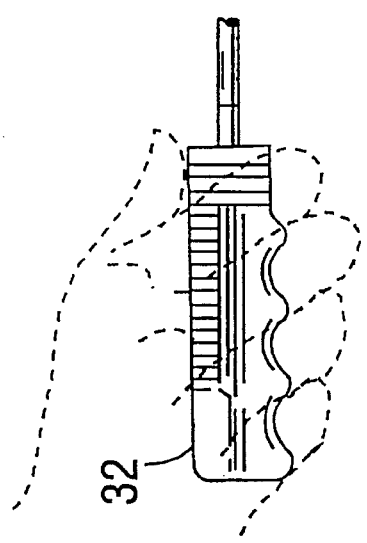
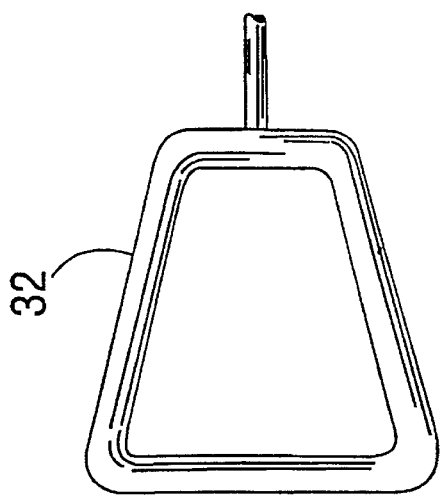
FIG. 14
FIG. 15

OBSTETRIC BONNET FOR ASSISTING CHILDBIRTH

This is a continuation of patent application Ser. No. 07/928,131, filed Aug. 10, 1992 issued May 16, 1996 as U.S. Pat. No. 5,507,752, which is a continuation of patent application Ser. No. 07/578,819, filed Sep. 6, 1990, now abandoned.

BACKGROUND OF THE INVENTION

1. Field of the Invention

The invention relates generally to obstetric traction delivery devices, such as forceps and vacuum cups, and more particularly to a flexible, collapsible bonnet which is manually placed over the top of the fetus' head and unrolled, stopping short of the eyes and ears. When pulled, the bonnet utilizes graded and limited friction and internally-created vacuum forces to secure itself to the fetus' head, thus allowing orientation and application of traction forces to the fetus.

2. Description of Prior Art

Presently, forceps and vacuum cup devices are used for assisting child delivery in difficult cases. Typical instances occur when the parturient force of the mother is not sufficiently strong, or when there is a need to maneuver the fetus for delivery. Forceps may be padded and are typically made from unyielding materials, such as stainless steel. When such rigid material is engaged against the soft, moldable fetal head, undesirable and potentially damaging compression may occur. A faulty application or incorrect use of forceps may not only injure the fetus, but may cause maternal injuries as well. Since present day obstetrical training programs tend to vary in their emphasis on forceps use, those who use forceps likewise vary in forceps use proficiency. The less the proficiency, the greater the risk that either fetal or maternal injuries may follow.

While there have been numerous forceps modifications to suit specific indications, the basic forces acting on the fetal head are the same regardless of the particular type of forceps used. Compression of the fetal head between the two blades of the forceps provides the necessary force as traction is being applied by the obstetrician to effect delivery. Excessive compressive and/or traction forces may cause trauma to the fetus and possibly the mother.

Obstetric vacuum cups have also been utilized in order to apply an externally created vacuum force to the head of the fetus and thus adhere a traction device to the fetus' head. In the past these vacuum cups were made of metal, and to facilitate entry into the vagina the metal cup had to be formed in a size comparably smaller than the head of the fetus. Recent vacuum cups have been manufactured from firm rubbery substances, which because of their modest deformability may be manufactured in larger sizes and still fit in the vagina. Nevertheless, all vacuum cup devices utilized or described in the literature require that the material substance of the cup be firm enough to prevent collapse when an external vacuum source is applied.

Vacuum cups work on the following principle: When air inside the cup is mechanically evacuated through tubing connected to the cup body, a portion of the fetal head tends to be drawn into the cup, thus attaching the cup to the fetus and allowing application of traction force through the cup to the fetus. Once the cup is attached, the fetus is then pulled out of the uterus of the mother. In a conventional construction of an obstetric cup, there has been a tendency of the fetal head, still weak in structural strength, to be sucked into the cup. This may result in the rupture of small blood vessels in the fetus' scalp. In addition, damage to the surface of the fetal head is possible because of the firm grip between the hard vacuum cup and the soft fetal scalp. Maternal damage such as lacerations and hematomas in vacuum cup deliveries is also possible if part of the maternal interior gets caught between the vacuum cup and the fetal head.

A problem with vacuum cups is that a practitioner needs to apply a higher vacuum force if higher traction forces are needed. The higher vacuum force keeps the cup adhered to the fetus' head when the cup is subject to higher traction force. Typical commercial vacuum cups allow for as much as six hundred mm (Hg) of vacuum to be achieved within the cup by either a handheld or electric vacuum pump. Higher vacuum pressures tend to increase the possibility that the fetus will sustain injury to the head. In addition, if too little vacuum force is applied and the cup abruptly disengages, then damage may also result to the fetus' head. Thus presently a vacuum cup practitioner is left with concerns that too much vacuum may deform the fetus' head, and too little vacuum may allow the cup to abruptly disengage from the fetus' head.

Other devices for facilitating fetal delivery have also been cited in the literature. A noose-type device designed to be connected to the fetal neck was shown by U.S. Pat. No. 1,782,814. A soft hood-type barrel-shaped vacuum device designed to enclose the entire fetal head was described in U.S. Pat. No. 2,227,673. A vacuum cup with bowl-shaped recesses, tubular passages incorporated into the cup walls, and utilizing the application of an external vacuum source was described in U.S. Pat. No. 3,765,408. A non-vacuum traction net was shown in U.S. Pat. No. 4,597,391.

In summary, known prior art is limited to three basic discrete modes of attaching an obstetric device to the fetus: compressive forces, externally applied vacuum forces, or noose/net-type attachments that tie a traction apparatus to the fetus. Only forceps and vacuum cups are in commercial use at this time. In general, use of these devices has resulted in an incidence of significant maternal trauma of 10–15%, and an incidence of fetal trauma of 10–20%.

No obstetric traction device currently utilized in medical practice may be used without relatively high risk of trauma to the fetus, the mother, or both. For this reason, use of obstetric traction devices has been limited to those situations where the risks of not using the device outweigh the substantial risk of trauma to the fetus, mother, or both. As a result, many deliveries are unduly time-consuming and painful. Moreover, many deliveries which could be achieved vaginally are presently taken to Cesarean section, greatly increasing the risks to the mother to avoid unknown risks to the fetus.

SUMMARY OF THE INVENTION

In one aspect, the present invention is specifically directed at reducing the high rates of maternal and fetal trauma associated with the use of existing obstetric traction devices. The obstetric bonnet of the invention helps to increase the safety of deliveries, to shorten normal delivery periods, and is superior to existing obstetric traction devices for use in difficult deliveries. In this way many deliveries may be shortened, lowering maternal pain, potential trauma to both the fetus and mother, and reducing the number of Cesarean section deliveries.

In a general aspect, the invention provides an attachment for the application of traction and rotational forces to a fetus that minimizes marks, bruises, lacerations, or vacuum injury to the fetus' head or to the mother.

An advantage of this invention is that it applies traction adhesion forces to a wide, dispersed surface area of the fetus' head in contrast to relatively concentrated forces of forceps and vacuum cups. Another advantage of this invention is that soft, disposable, traction devices may be produced in varying sizes and shapes for differing degrees of fetal molding and head sizes.

Preferred embodiments of this invention provide sanitary, light, and inexpensive traction devices that may be easily transported and stored in a sanitary condition, and thus be available for use in remote areas.

Embodiments of this invention also provide advantages in that they do not require an external pump for the creation and maintenance of a vacuum adherence force. The invention is thus easier and simpler to make, use, and learn how to use, as well as being safer.

With the present invention less vacuum forces are required (and thus less fetal deformation will occur) because friction forces help adhere the bonnet to the fetus' head. Fetal head deformation is also reduced because the flexible, collapsible bonnet, unlike firmer presently-used vacuum cups, molds to fit the fetus' head.

The invention is more readily acceptable by patients because of the substantial elimination of the need for the usage of hard, metal instruments or connection of the patient to an external suction machine. Another advantage of this invention is that it is designed to absorb excessive longitudinal force exerted by a practitioner without breakage within the mother.

This invention may be used to apply fetal monitoring devices for monitoring the fetus during delivery. This invention also reduces the actual time consumed in the delivery of a fetus, by providing a safe method of applying traction force to aid the mother in delivery.

Other uses and advantages of the present invention will be apparent to one skilled in the art upon examination of the accompanying description in conjunction with the drawings.

The above-mentioned and other advantages of the present invention may be achieved by a flexible, smooth, collapsible obstetric bonnet that is fitted on a fetal head and has adherence thereto because of frictional and vacuum-related forces. The bonnet comprises a smooth, elastic, collapsible dome or cylinder that is contoured to fit the fetal head with a substantially skin-tight, substantially airtight fit. The dome or cylinder has an open end and a closed end. The dome or cylinder preferably has a rounded raised lip on the outer surface edge of the open end and may have a mechanical extension fixed or detachably attached to or near the apex of the outer surface of the closed end. A firm disc may be incorporated into the closed end of the dome or cylinder.

The walls of the dome or cylinder are comprised of a smooth, elastic, substantially air-impermeable material such as latex rubber or another elastomer, and the wall interior may be reinforced with an elastic mesh such as nylon. The bonnet material should be sufficiently air-impermeable so that a vacuum force is generated when a fitted bonnet is pulled after application to the fetus' head. The walls are tapered to provide a varying amount of surface area in snug contact with the fetal head.

Although the bonnet is comprised of a substantially air-impermeable material, that material may be manufactured to purposely leak, for example because of material stretching, when a calibrated excessive or limiting force is applied to the bonnet. This feature may be an important safety feature to prevent excessive force being applied to the fetus. In operation, a bonnet so modified would work as described below, except that when a calibrated force is exceeded, the bonnet leaks, the vacuum loses force, and the bonnet slowly slides off the fetus' head. The slow sliding of the bonnet off the fetus' head should prevent any damage that might be caused by an abrupt dislocation of the bonnet.

In an important embodiment, a connection may be attached to the outer surface of the closed end of the bonnet. The connection may be made with fittings for the attachment of a mechanical extension to the bonnet. Alternately, the mechanical extension may be directly fixed to the bonnet—i.e. without a separate connection.

To protect against injury to the fetus, the bonnet may incorporate a strain gauge separately or with the mechanical extension. This strain gauge may be calibrated to exhibit a warning to the practitioner when excessive force is being applied.

A mechanical extension fixed or otherwise attached to the bonnet or the connection on the closed end of the bonnet may be made to irreversibly stretch, thus alerting a practitioner when a limiting or excessive longitudinal force is being applied. The mechanical extension may be modified to allow rotational force to be applied to the fetus. It may comprise of a handle, grommet, rope, cord, flexible member or any other structure that enables the practitioner to grasp the bonnet. The mechanical extension may also comprise a substance such as rope, plastic or metal, and may be coated with a non-elastic paint or plastic that will crack or break and thereby warn a practitioner when limiting or excessive longitudinal force is applied. Fetal monitoring devices may also be attached to the connection on the closed end of the bonnet. Alternatively, the mechanical extension or the fetal monitoring devices may be directly attached to the bonnet itself.

In a preferred embodiment, the bonnet may be utilized in the following manner: (1) the fetal head is measured by ultrasound, (2) an appropriately sized bonnet is chosen, (3) the bonnet is collapsed, rolled, and inserted into the birth canal and placed on top of the fetal head, (4) the bonnet is unrolled over the fetal head, stopping short of the eyes and ears, (5) the bonnet's mechanical extension is pulled to effectuate an internally-created or self-induced vacuum between the bonnet and the fetus' head, (6) the mechanical extension is pulled or rotated to remove or turn the fetus, and (7) once birth is complete, the bonnet is removed by rolling its edges over the baby's head.

In one embodiment the bonnet may be manufactured in the following manner: (1) an appropriately sized non-adhesive mold is selected, (2) the mold is wrapped with a bonnet reinforcing material such as nylon mesh, cloth, fabric, or film, and all desired attachments such as a grommet, handle, firm disk, connection, etc. are attached, (3) the mold is then immersed into an emulsion of liquid, elastomeric material such as latex rubber or silicone rubber that hardens when dried to form a flexible and substantially air-impermeable structure, (4) the mold is allowed to dry and the material is removed from the mold, (5) the material is dipped and dried again and again in the liquid, elastomer until the desired material thickness is achieved, and (6) optionally, the material is heated until the elastic material is stabilized. The thickness of the walls of the bonnet is controlled by the concentration of the liquid elastomer, the immersion time, and the numbers of immersions. Certain embodiments will only require one dipping to achieve sufficient wall thickness.

Other embodiments of the bonnet may be manufactured by injection molding or other equivalent manufacturing techniques. It is envisioned that in at least one embodiment the bonnet will be manufactured with strain gauges and a permanent mechanical extension such as a cord, a looped cord, or a two-finger handle connected to it. These embodiments may be manufactured in such a way that the mechanical extension is connected either before or after the bonnet is immersed into a liquid, elastic material.

BRIEF DESCRIPTION OF THE DRAWINGS

FIGS. 1 and 2 are isometric drawings of opposite ends of a bonnet embodiment.

FIG. 1A is an isometric drawing of detachable mechanical extension for the bonnet in FIGS. 1 and 2.

FIGS. 14 and 15 show two embodiments of mechanical extensions incorporated with safety and force monitoring devices.

Figure 3:
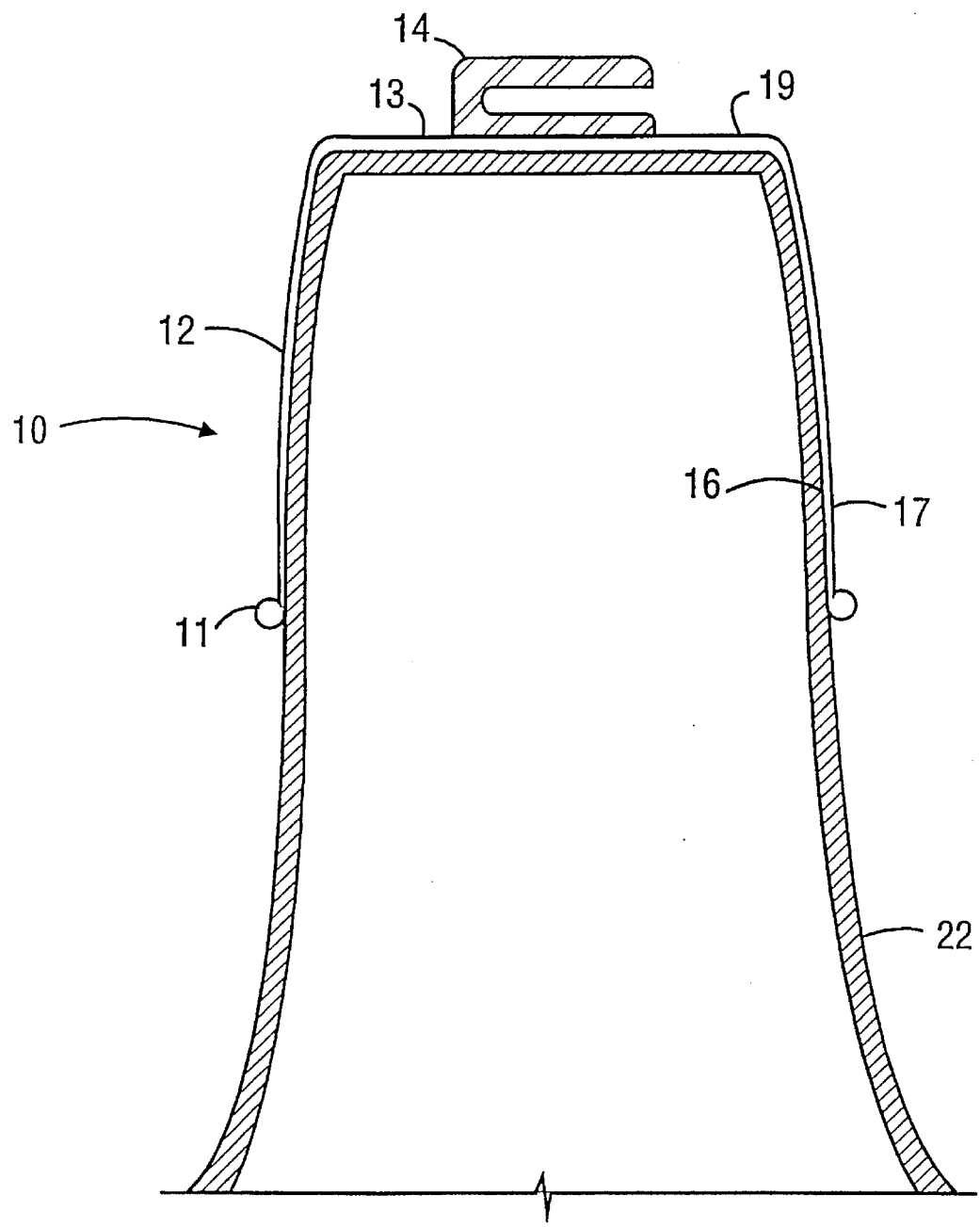
FIG. 3 provides a cross-sectional view of a bonnet as it is being constructed.

None of the above drawings are drawn to a precise scale.

DESCRIPTION OF PREFERRED EMBODIMENTS

FIGS. 1 and 2 show one preferred form of the obstetric bonnet 10 of the invention. The bonnet 10 is dome-shaped, but it is envisioned that cylinder shapes and other suitable forms with one closed end and one open end may be employed. Referring to FIGS. 1 and 2, the bonnet 10 comprises a flexible, smooth, collapsible, dome-shaped wall 12 with an inner surface 16, an outer surface 17, a raised lip 11 on the open end 20, and a firm disk 13 on the closed end 19.

In a preferred embodiment the raised lip 11 on the open end 20 is rounded to provide a smooth surface to contact the interior of the mother. Other shape modifications of the raised lip 11 are possible. In general, the bonnet is shaped to encase the head of a fetus down to the eyes and ears.

The firm disk 13 is preferably incorporated into the material of the closed end 19 and serves to stiffen the closed end 19. Stiffening the closed end 19 of the bonnet 10 is not absolutely necessary but doing so facilitates attachment of the connection 14 and helps to provide support to the overall collapsible character of the bonnet. It thus prevents total collapse of the bonnet which is important in forming the bonnet vacuum during use. It is envisioned that bonnets will be manufactured without the firm disk 13 for some applications. Alternately, the size of the firm disk 13 may be varied to provide different support levels to the bonnet 10. The firm disk 13 preferably comprises a firm piece of flexible silicon rubber cut in a coin shaped pattern. Other materials and shapes are possible for the firm disk 13 and such materials and shapes are contemplated by this disclosure to the extent that they provide the firm support required in this application. The firm disk 13 can be described as a means for supporting the closed end 19 or the bonnet 10 and includes other embodiments such as a stiffened closed end 19 or ribbed support in the closed end 19.

The inner surface 16 is contoured or configured near the open end 20 to match the shape of a fetus' head. Some bonnets may be manufactured without contouring without detracting from the overall conception of the bonnet 10 disclosed here. It is necessary that at least some part of the bonnet 10 near the raised lip 11 provide a snug contact between the fetus' head 9 and the bonnet 10. In one preferred embodiment at least two centimeters of the interior circumference of the inner surface 16 (i.e., about a two-centimeter band) is in snug contact with the fetus' head 9 (see e.g., FIGS. 4–6). The amount of snug contact may vary depending on the application. "Snug" as used in this disclosure means substantially skintight and substantially air impermeable.

The firm disk 13 has a slotted connection 14 or other suitable connection 14 attached to it which may be used for the attachment of a mechanical extension. As shown in FIGS. 1 and 1A, mechanical extension 15 is connected to the bonnet 10 by sliding the mechanical extension connector 18 into the connection 14. The connection 14 and mechanical extension connector 18 depicted in FIGS. 1, 1A and 2 are but one of many possible configurations for a connection point. The connection 14 and the mechanical extension connector 18 may be generally described as a means for connecting attachments to the bonnet 10. Thus "means for connecting attachments" in the context of this disclosure includes threaded, snap-on, clip-on, slotted, and any other suitable type of connecting mechanism.

In one preferred embodiment, the connection 14 and mechanical extension connector 18 are omitted and the mechanical extension 15 is directly attached to the bonnet 10. Other similar modifications may be incorporated into the bonnet 10 and still be within the scope of the invention disclosed here.

In one preferred embodiment the wall 12 comprises a thin nylon base coated on both sides with latex rubber or silicon rubber. The nylon serves as a reinforcing material to support the walls of the bonnet. "Reinforcing material" in this context means any suitable material that will help support the structure of the bonnet. The reinforcing material is optional, since a suitable bonnet may be manufactured without it. In addition, the bonnet walls 12 may also be coated with any elastic, collapsible material that is smooth and substantially air impermeable. Such materials would include but not be limited to latex rubber, silicon rubber, natural rubber, polyvinyl, plastic, polyethylene, or an elastomer. "Elastomer" refers to an organic-based material that is a solid at ambient temperatures and has some degree of elasticity associated with it. Suitable reinforcing materials are contemplated to include nylon mesh, fiber, clothing and film.

During construction of the bonnet 10, the firm disk 13 may be incorporated into the walls 12 of the bonnet 10. The connection 14 is then attached to the firm disk 13 or otherwise incorporated into the material of the walls 12. If the bonnet is to be constructed directly attached to a mechanical extension 15, then the mechanical extension is attached to the outside of the closed end 19 in lieu of or in addition to the connection 14.

The raised lip 11 comprises a thin, elongated flexible cylinder-shaped piece of silicon rubber or any stiff flexible smooth material that will serve for this purpose. The raised lip 11 is also attached to the walls 12 or incorporated into the material of the walls 12. An alternate method of forming the raised lip 11 comprises dipping the mold beyond the contemplated length of the bonnet and then rolling the excess length to the dimension desired before the coating material has completely dried. It is an important part of the bonnet as it facilitates rolling the bonnet. The raised lip 11 also serves to strengthen the walls 12 or the edge of the walls 12, and may add elasticity to the walls 12, or edge of the walls 12. It may also strengthen the substantially airtight seal on the edge of the walls 12. The raised lip 11 can be generally referred to as a means for grasping the bonnet 10 and includes other embodiments such as grommets, ribs, bulges, or specialized roughened areas in the bonnet walls 12 that facilitate grasping the bonnet 10.

Referring to FIG. 3, in this preferred embodiment the raised lip 11 is woven into the wall 12 nylon base. The connection 14 is also woven or otherwise attached to the walls 12. After the reinforcing material has been attached to the firm disk 13, the raised lip 11, and connection 14, the resulting apparatus is referred to as a "bonnet base." In this context, "bonnet base" means an incomplete bonnet during construction. It is also envisioned that the bonnet may be constructed by attaching the raised lip 11, the firm disk 13, a mechanical extension 15, or the connection 14 after the walls 12 are completed.

An appropriately shaped mold 22 is optionally coated or wrapped with a non-stick material such as cloth, paper, polyester, nylon or a lubricant. "Non-stick" in this instance means sufficient insulation of the bonnet 10 from the mold 22 so that the bonnet 10 does not stick to the mold 22 during the manufacturing process. A non-stick material is not required if the mold 22 already includes a non-stick surface such as glass, stainless steel, or a similar material.

The walls 12 are fitted over an appropriately shaped mold 22. The mold 22 and bonnet base are dipped into a molten coating material bath and dried or allowed to dry, thus covering these parts with a smooth, elastic coating. In one preferred embodiment, the coating material is latex rubber or silicon rubber. The coating materials permeate the reinforcing material and provide a smooth surface on both the inside and outside of the bonnet 10. The bonnet 10 may be dipped and dried repeatedly until the coating material desired thickness is achieved. In the preferred method, the thickness of the walls 12 is controlled by varying the immersion time or the concentration of the coating material. In this manner the bonnet need only be dipped once to achieve the desired wall thickness.

Optionally, the entire bonnet 10 is then subjected to heat for approximately twenty minutes at 250° F. and allowed to cool. Varying amounts of heat and heating times may be employed to stabilize the bonnet 10, depending on the types of material used and the degree of stabilization desired. Subjecting the bonnet to heat allows the coating material to stabilize. Depending on the type of coating material used, the heat process may or may not be necessary. Silicon rubber is a preferred coating material if the bonnet will be subjected to heat during any stabilization or sterilization processes.

An alternate method of manufacturing the bonnet 10 includes using an injection molding process to form the bonnet 10. It is envisioned that injection molds may be procured that will match the size and shape of a desired bonnet 10. Attachments such as a firm disk 13, rased lip 11, connection 14, or mechanical extension 15 can be formed as part of the injection molding process or attached to a bonnet 10 by glue of heat-sealing after the bonnet 10 is formed. Stabilization of the bonnet 10 can be achieved with a bonnet 10 created by injection molding in the same manner as other stabilization processes.

Figure 4:
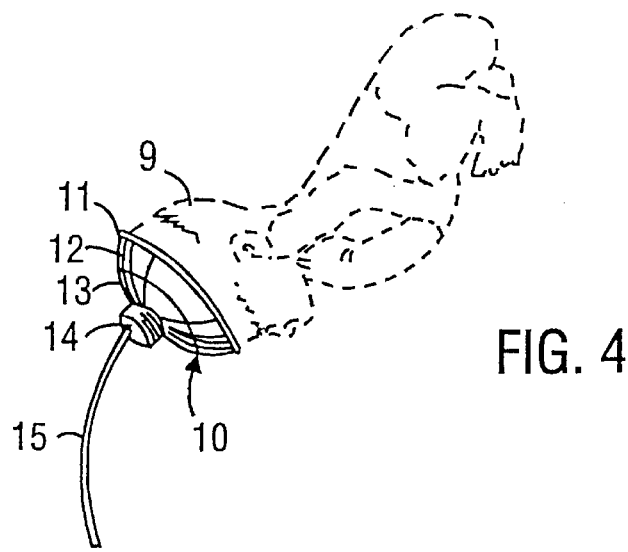
FIGS. 4, 5, and 6 show a bonnet as it is being applied to a fetus.
Figure 5:
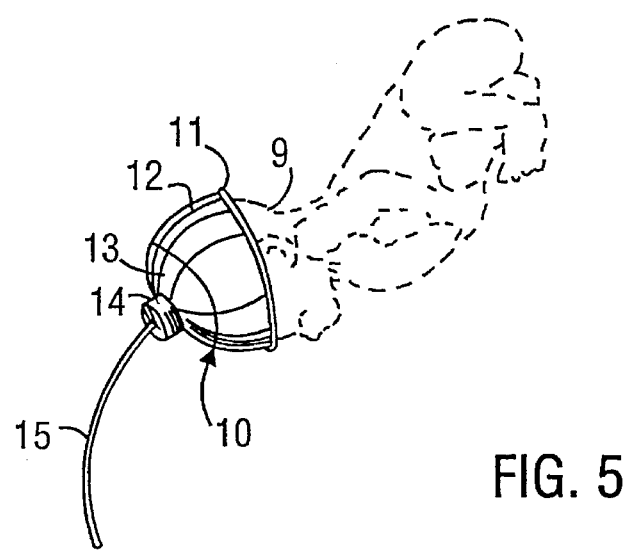
Figure 6:
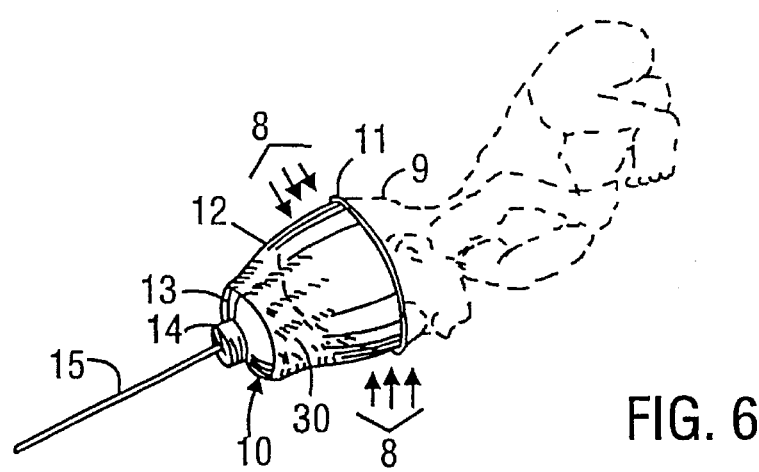
Figure 7:
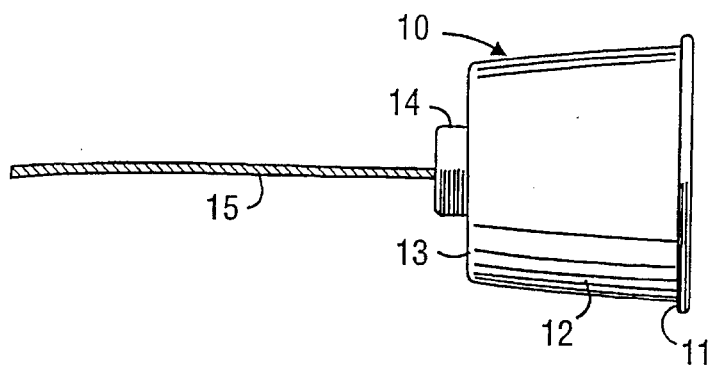
FIGS. 7, 8, 9, and 10 depict a side view of a bonnet with various embodiments of simple mechanical extensions attached.
Figure 8:
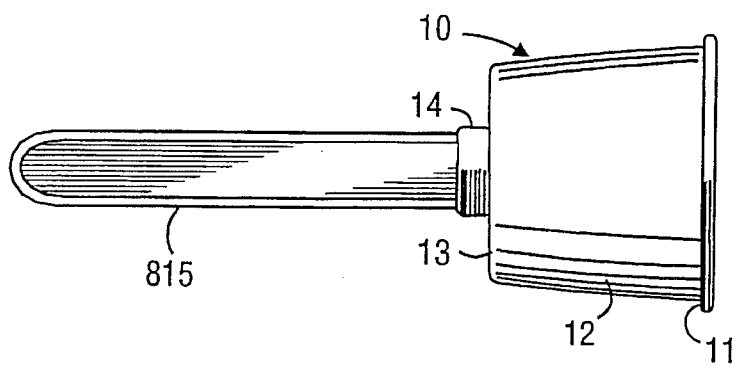
Figure 9:
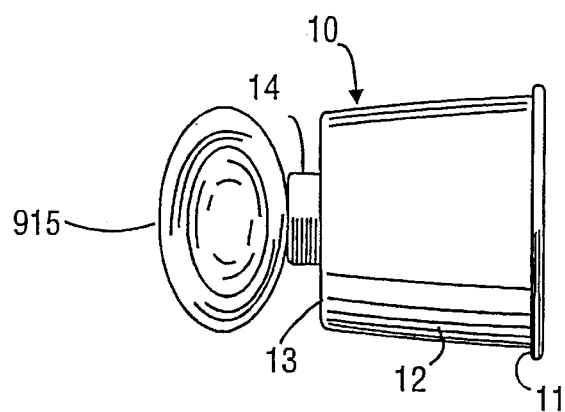
Figure 10:
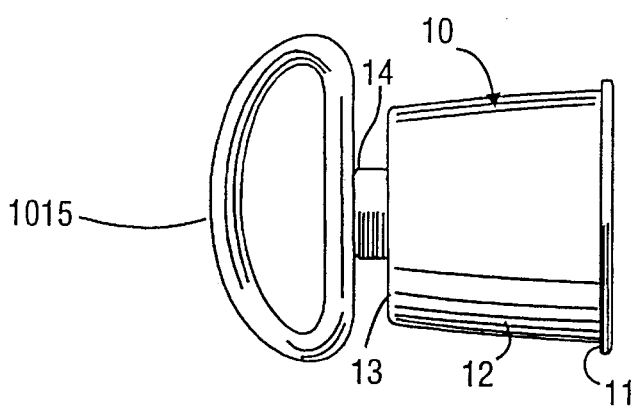

FIGS. 4, 5, and 6 show the bonnet as it is placed on a fetus. "Fetus" as used in this description means an unborn infant still fully or partially within the mother. The bonnet 10 is preferentially utilized by first sizing the fetus' head 9 using ultrasound or other techniques. It is envisioned that differently sized bonnets will be previously made and available to the practitioner. Alternately, the bonnet is relatively easy to construct and therefore, if time allows, practitioners may have bonnets created to exactly fit each fetus.

Once the fetus' head 9 is sized, an appropriate bonnet 10 is selected and collapsed before insertion into the vagina. The walls 12 of the bonnet 10 are thin enough such that the bonnet 10 easily collapses upon itself. Once inserted, the bonnet 10 is manually fitted over the top of the fetus' head 9 by rolling and stretching the bonnet walls 12 towards the brow and ears of the fetus.

FIG. 4 shows the bonnet 10 as it is initially placed and applied to the fetus' head 9. The raised lip 11 is used as a means for grasping the bonnet 10 and to help position the bonnet 10 on the fetus' head 9. As shown in FIG. 5, the bonnet 10 is fitted to the fetus' head 9 until it reaches the top of the brow and above the ears. The firm disk 13 serves as a means for supporting the bonnet 10 and for distributing the forces applied to the bonnet.

Once fitted, the bonnet 10 provides a near skin-tight, substantially airtight seal onto the fetus' head 9. Applying longitudinal force utilizing a mechanical extension 15 as shown in FIG. 6 distorts the bonnet's 10 shape, increasing the free space 30 between the bonnet 10 and the fetus' head 9, thus creating a vacuum adhesion force to the fetus' head 9 (represented by the force arrows 8 in FIG. 6). In addition, applying a longitudinal force longitudinally stretches the bonnet 10 and decreases the bonnet 10 diameter, thus further increasing the forces between the bonnet 10 and the fetus' head. Adhesion of the bonnet 10 is also enhanced by frictional forces caused by the tight circumferential fit between the bonnet 10 and the fetus' head 9. The use of the friction in conjunction with internally-created vacuum forces is one feature that differentiates the bonnet from any such apparatus previously described.

Once the fetus is removed, the bonnet 10 is removed by manually rolling it, starting with the raised lip 11 and rolling the bonnet 10 towards the closed end 19.

Figure 11:
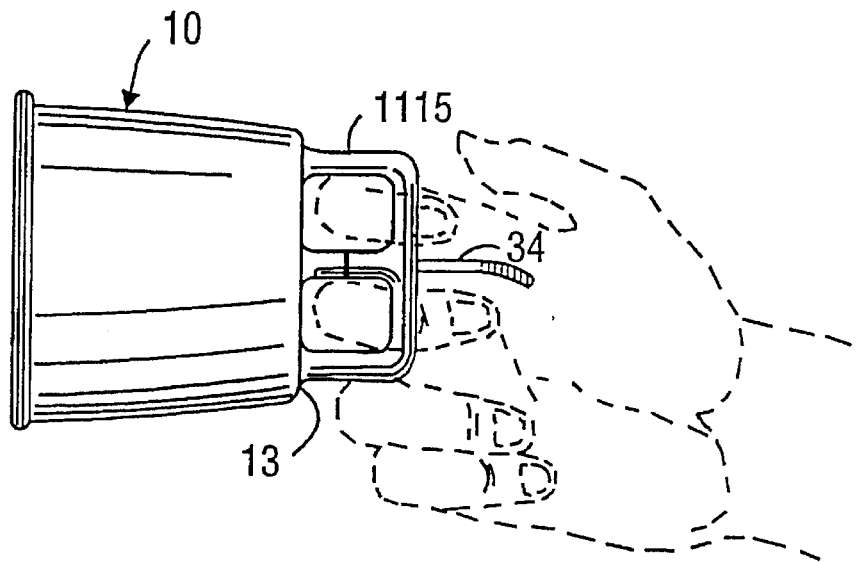
FIGS. 11 and 12 show a two-fingered handle mechanical extension with a strain gauge.
Figure 12:
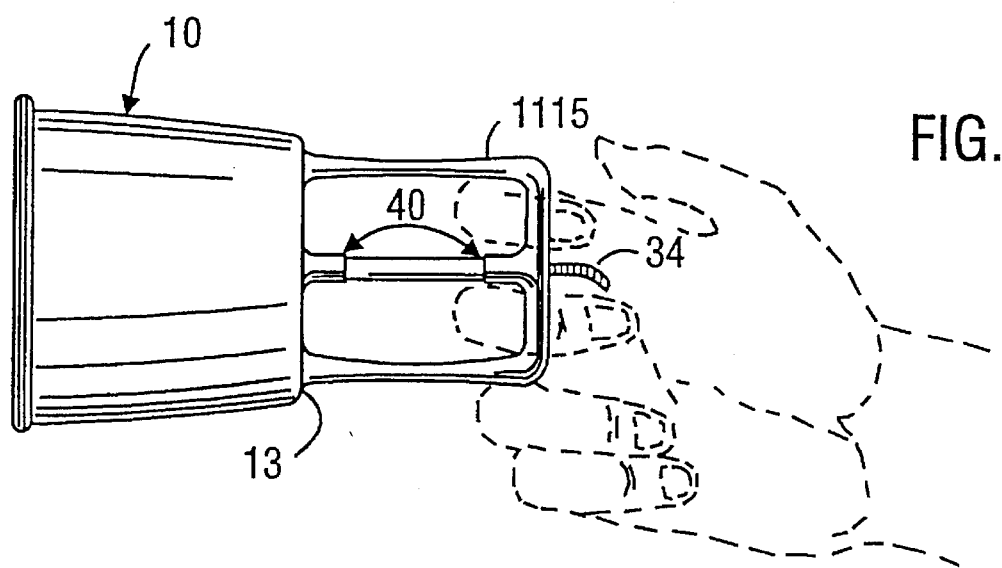
Figure 13:
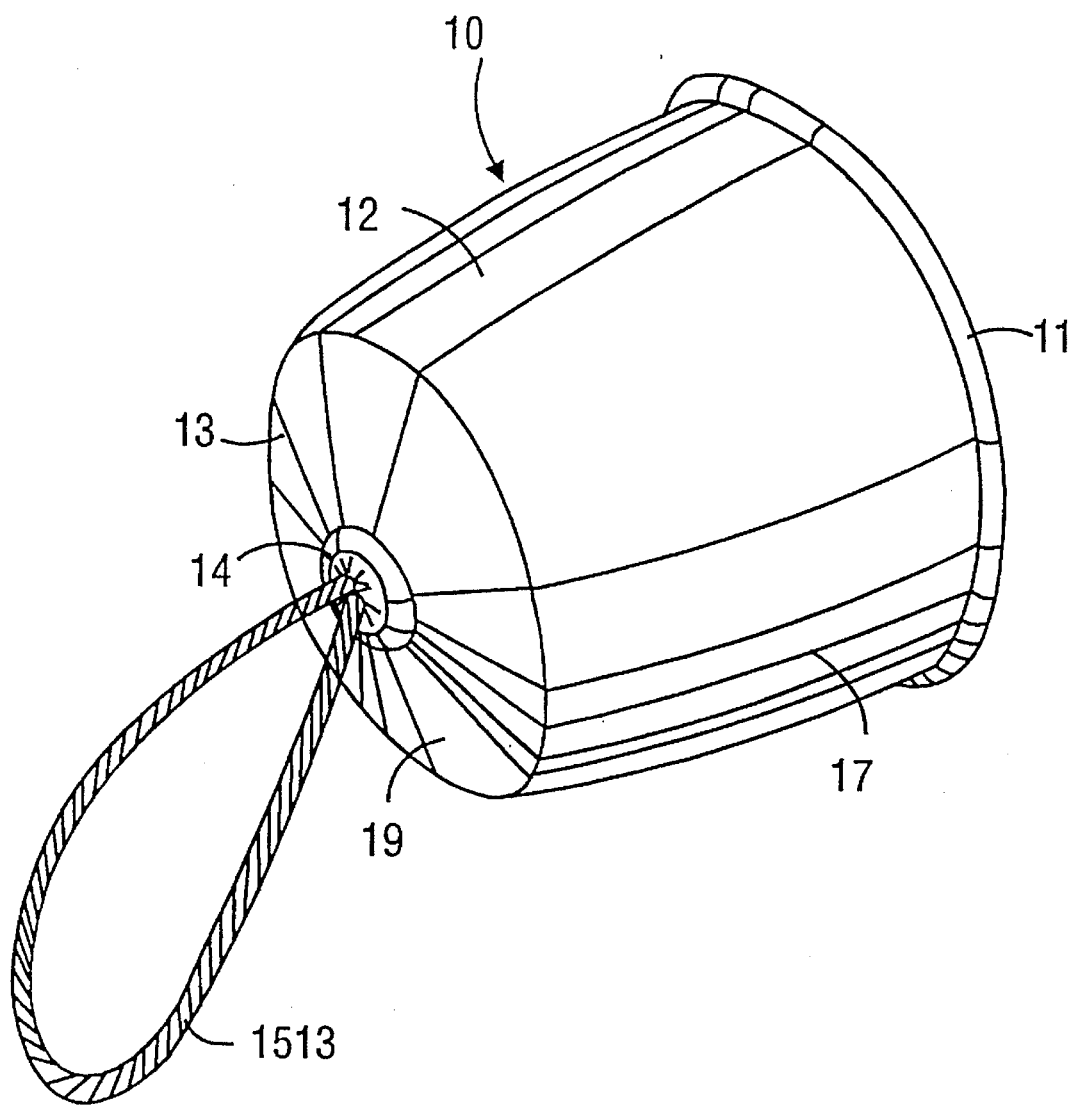
FIG. 13 shows a looped cord mechanical extension permanently attached to the bonnet.
Figure 16:
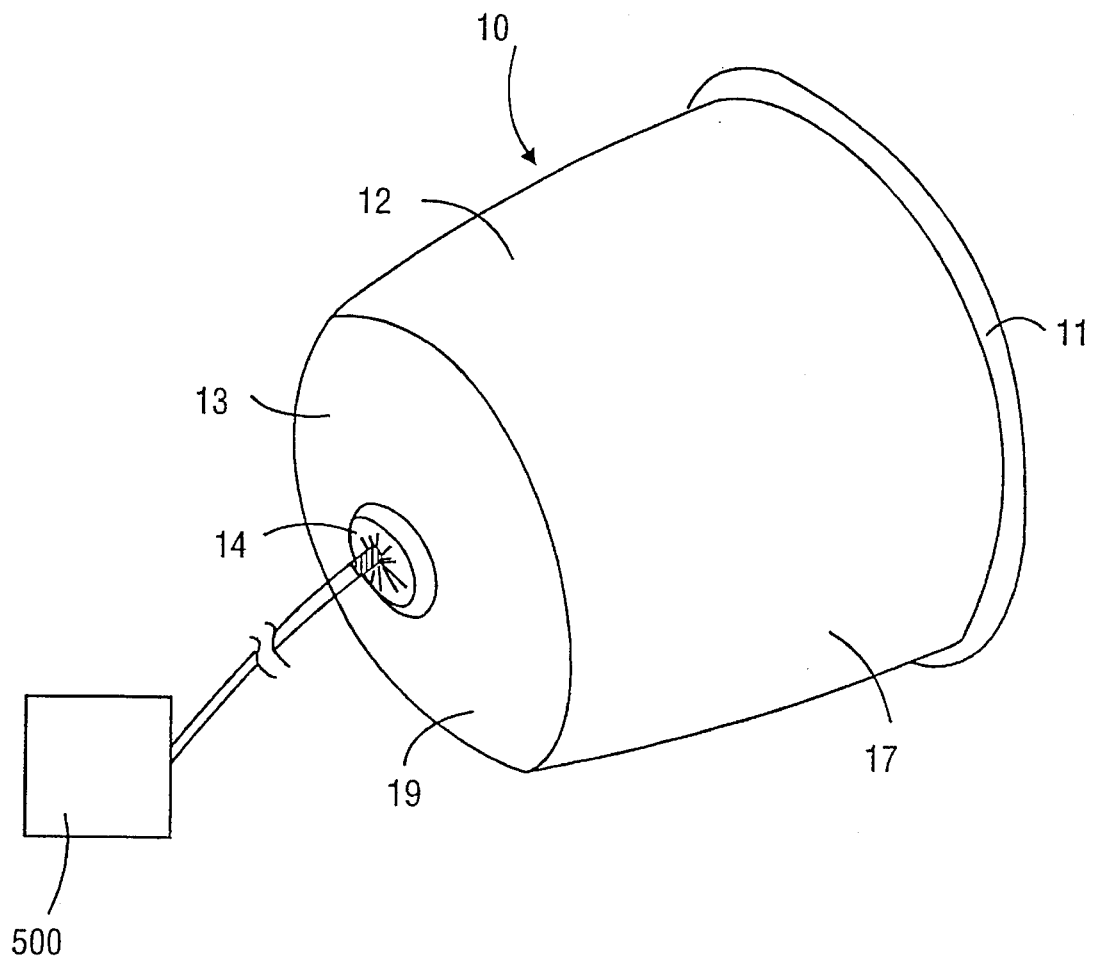
FIG. 16 shows a bonnet attached to a fetal monitoring device.

Depending on the type of mechanical extension 15 used, the practitioner may either apply rotational and/or longitudinal force to reposition or apply traction force to the fetus. "Mechanical extension" as used in this disclosure means any object attached to the bonnet or to the connection 14 of the bonnet that may be grasped by the practitioner. FIGS. 7, 8, 9, and 10 show a bonnet 10 with alternate forms of mechanical extensions. Depending on the application, the mechanical extension be constructed to be a simple cord or cable as in FIG. 7, a long thin handle as in FIG. 8, a grommet attachment as in FIG. 9, or a handle as in FIG. 10. "Grommet" as used in this specification means any short extension or "ear" of material connected to the connection 14 which a practitioner could grasp. FIGS. 11 and 12 show a two-finger handle type of mechanical extension 1115. FIG. 13 shows a loop-type mechanical extension 1513 in the form of a cord permanently attached in a loop fashion to the bonnet 10. The mechanical extension may comprise rope, plastic, metal, rubber, or an elastomer.

In addition, a strain gauge 34 may be incorporated into the mechanical extension 15 or the bonnet 10 itself. This gauge 34 would serve as signal means to alert the practitioner as to the amount of force being applied to the bonnet 10. The gauge 34 may also alert the practitioner when an excessive force was being applied. A strain gauge 34 may be mechanical or electrical, or any other readily available force measuring device. In it's simplest mode, the strain gauge 34 may be a simple cord attached to the bonnet 10 with a marked area on the cord to indicate excessive force. See FIGS. 11 and 12. The strain gauge 34 shown in FIGS. 11 and 12 is calibrated in conjunction with a flexible mechanical extension 1115 to alert the practitioner when the mechanical extension 1115 is flexed a calibrated amount 40. The amount of flexing in the mechanical extension is calibrated in conjunction with the strain gauge 34 length.

Modifications of the presently described mechanical extensions 15 are possible without detracting from the inventions as disclosed here. For instance, it is possible to directly connect the mechanical extension 15 without the use of the connection 14 or the mechanical extension connector 18.

In one embodiment, the mechanical extension 1514 may be modified to avoid applying too much force. FIG. 14 shows a mechanical extension 1514 that is partially constructed of metal 30 calibrated to irreversibly bend and lengthen when an excessive force is applied. This built-in safety feature allows the practitioner to modify the delivery method if the mechanical extension 1514 shows that too much force was being applied to the fetus. The lengthening of the metal 30 serves to alert the practitioner. Furthermore, the mechanical extension 1514 may also be painted such that when the metal 30 stretches a desired length, the paint cracks, thus alerting the practitioner.

FIG. 14 is a drawing of a mechanical extension 15 equipped with a practitioner handle 32, a strain gauge 34, and connections 28 to connect the mechanical extension 1514 to the bonnet 10. The mechanical extension 1514 is preferentially constructed to yield instead of failing when excessive force is applied, thus avoiding fetal trauma caused by sudden mechanical extension failure. The mechanical extension 1514 is designed to bend at a force much lower than the force necessary to tear any of the components in the body of the bonnet 10.

Should the mechanical extension 1514 bend or be otherwise unfit, it may be removed and a new mechanical 1514 extension applied by unfastening the mechanical extension connector 18 while the bonnet is still adhered to the fetus' head. It is sometimes easier to change the mechanical extension 1514 in place than to remove the entire bonnet 10 and start again. It is envisioned that practitioners may routinely switch mechanical extensions and/or fetal monitoring devices (see discussion below) in situ.

FIG. 15 is a drawing of an alternate embodiment of the mechanical extension 1515. FIG. 15 shows a mechanical extension 1515 with a practitioner handle 32, mechanical extension connector 18, a force gauge 34, and a series of tapered interfitting sections 36. The series of tapered interfitting sections 36 are designed in the manner of a telescope such that each section is molded to slide out of the next section. The sections sliding out of each other alert a practitioner at a predetermined force.

Any of the mechanical extensions may be fitted to the bonnet 10 with mechanical extension connectors 18 that are threaded, mechanical snap-on, clip-type connections, or by simply tying the extension to the bonnet 10. The bonnet 10 may be built to connect with different types of removable mechanical extensions.

The bonnet 10 may be built to incorporate fetal monitoring devices 500 that would provide feedback on the condition of the fetus before and during delivery. It is contemplated that fetal monitoring devices may be attached to the bonnet 10 in the same manner as and/or in conjunction with a mechanical extension. It is contemplated that the bonnet 10 will be constructed to provide a hole, if necessary, to facilitate contact between the fetus 9 and the monitoring device. The substantially airtight nature of the bonnet 10 may be maintained by providing connections that are substantially airtight. It is envisioned that the fetal monitoring devices will be used in conjunction with a mechanical extension. Fetal monitoring device wires may be provided in an annulus within the mechanical extension. Non-limiting examples of fetal monitoring devices include an oximeter or a fetal scalp electrode.

The walls 12 of the bonnet 10 are substantially airtight. Latex rubber has been utilized in the preferred embodiment. Other components such as silicon rubber, natural rubber, polyvinyl, plastic, polyethylene, or an elastomer are contemplated to also work adequately for the bonnet 10. It is expected that persons skilled in the art may adapt still other substances that will work well in this utility since it is essential only that the walls 12 be made of a flexible, collapsible, smooth material that will be substantially airtight and flexible enough to conform to the fetus' head. "Substantially airtight" in this context does not necessarily mean completely airtight. In this context it is enough that the material will temporarily prevent substantial air transfer to the free space 30 between the bonnet 10 and the fetus' head 9, thus allowing a temporary vacuum force to be created in the free space 30 within. As previously discussed, some bonnets 10 may be constructed to leak when a predetermined longitudinal force is applied to the bonnet, thus allowing the bonnet 10 to slide off the fetus' head without causing damage. In addition, the material needn't be completely "smooth." "Smooth" in this context simply means smooth enough to provide a non-abrasive surface to the fetus' head 9 and to the interior of the mother.

Further modifications and alternative embodiments of the apparatus of the invention will be apparent to those skilled in the art in view of this description. Accordingly this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size and arrangements of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

Changes may be made in the parts, elements and assemblies described herein or in the steps or the sequence of steps of the methods described herein without departing from the spirit and scope of the invention as defined in the following claims.

What is claimed is:

1. An obstetric bonnet shaped to snugly encase a fetal head down to about eyes and ears, the bonnet being formed from a soft, flexible and substantially air-impermeable sheet of material, such that, when emplaced, the bonnet has frictional and substantially airtight adherence to the fetal head, the bonnet defined further as comprising a means for applying force to move a fetus and wherein the bonnet leaks when a predetermined stretching force is applied to the bonnet.

2. The obstetric bonnet of claim 1 further comprising a gauge for measuring the amount of force applied to the bonnet.

3. The obstetric bonnet of claim 1 defined further as comprising a fetal monitoring device.

4. The obstetric bonnet of claim 1 further comprising an oximeter or fetal scalp electrode.

5. The obstetric bonnet of claim 1 further comprising signalling means responsive to a predetermined longitudinal or rotational force.

6. An obstetric traction delivery apparatus, comprising:

a smooth, collapsible bonnet shaped to provide a snug fit to a fetal head down to about eyes and ears, said bonnet having an inner surface, an outer surface, an open end with an edge, a closed end, walls, and a fixed or detachable mechanical extension, wherein said bonnet walls are formed from substantially air-impermeable material and, when fitted on a fetal head, provide substantial adherence thereto because of frictional forces and a substantially airtight fit and, when a predetermined stretching force is applied to the bonnet, said walls become air permeable and leak to lessen frictional and vacuum-related forces.

7. The apparatus of claim 6 wherein the mechanical extension comprises a handle.

8. The apparatus of claim 6 further comprising signalling means responsive to a predetermined longitudinal or rotational force.

9. The apparatus of claim 6 further comprising a gauge for measuring the amount of force applied to the bonnet.

10. The apparatus of claim 6 further comprising at least one fetal monitoring device.

11. The apparatus of claim 10 wherein the fetal monitoring device is attached to the bonnet by means of the mechanical extension.

12. The apparatus of claim 10 wherein said monitoring device is a fetal scalp electrode or an oximeter.

13. An obstetric traction delivery apparatus, comprising:

a smooth, collapsible bonnet shaped to provide a snug fit to a fetal head down to about eyes and ears, said bonnet having an inner surface, an outer surface, an open end with an edge, a closed end, walls, a fixed or detachable mechanical extension, and a fetal monitoring device, wherein said bonnet walls are formed from substantially air-impermeable material and, when fitted on a fetal head, provide substantial adherence thereto because of frictional forces and a substantially airtight fit and, when a predetermined stretching force is applied to the bonnet, said walls become air permeable and leak to lessen frictional and vacuum-related forces.

14. The apparatus of claim 13 wherein the fetal monitoring device is attached to the bonnet by means of the mechanical extension.

15. The apparatus of claim 13 wherein said monitoring device is a fetal scalp electrode or an oximeter.

\* \* \* \* \*